(12) United States Patent
Kosierkiewicz (10) Patent No.: US 9,586,038 B1
(45) Date of Patent: *Mar. 7, 2017

(54) SYSTEM AND METHOD FOR A DRY ELASTOMER ELECTRODE

(71) Applicant: Tomasz Andrzej Kosierkiewicz, Mount Vernon, IL (US)

(72) Inventor: Tomasz Andrzej Kosierkiewicz, Mount Vernon, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/019,114

(22) Filed: Sep. 5, 2013

Related U.S. Application Data

(63) Continuation-in-part of application No. 13/020,392, filed on Feb. 3, 2011, now Pat. No. 8,569,935, which is a continuation-in-part of application No. 12/835,972, filed on Jul. 14, 2010, now abandoned, and a continuation-in-part of application No. 12/559,061, filed on Sep. 14, 2009, now abandoned.

(60) Provisional application No. 61/788,575, filed on Mar. 15, 2013, provisional application No. 61/819,574, filed on May 4, 2013, provisional application No. 61/347,963, filed on May 25, 2010.

(51) Int. Cl.
*A61N 1/05* (2006.01)
*A61N 1/04* (2006.01)
*A61B 5/04* (2006.01)

(52) U.S. Cl.
CPC ............ *A61N 1/0488* (2013.01); *A61B 5/04* (2013.01); *A61N 1/0484* (2013.01)

(58) Field of Classification Search
CPC . A61N 1/04; A61N 1/06; A61N 1/375; A61N 1/0404; A61N 1/042; A61N 1/0424; A61N 1/0436; A61N 1/044; A61N 1/0452; A61N 1/0456; A61N 1/046; A61N 1/048; A61N 1/0484; A61N 1/0492; H05K 1/00
USPC .................................... 607/149, 152
See application file for complete search history.

(56) References Cited

U.S. PATENT DOCUMENTS

| | | | | |
|---|---|---|---|---|
| 1,989,282 | A * | 1/1935 | Kimble et al. | 607/152 |
| 5,038,796 | A * | 8/1991 | Axelgaard et al. | 607/152 |
| 5,520,683 | A * | 5/1996 | Subramaniam | A61N 1/0492 606/32 |
| 6,544,258 | B2 * | 4/2003 | Fleenor et al. | 606/32 |
| 2005/0015134 | A1 * | 1/2005 | Carim | 607/142 |
| 2008/0033506 | A1 * | 2/2008 | Flick | 607/50 |

OTHER PUBLICATIONS

Pylatiuk et al, "Comparison of Surface EMG Monitoring Electrodes for Long-term Use in Rhabilitation Device Control", Jun. 2009, IEEE 11th International Conference on Rehabilitation Robotics, 9781-4244-3789-4; pp. 300-304.

(Continued)

*Primary Examiner* — Edward Moran
*Assistant Examiner* — Elizabeth K So
(74) *Attorney, Agent, or Firm* — Jessica W. Smith; Loza & Loza LLP (57) ABSTRACT

A stimulation or recording electrode with varying impedances includes a plurality of layers that are compressed together with varying compressions forces, with at least a first compression force used at the perimeter of the electrode and a second compression force used towards the center of the electrode, with the first force being lesser than the second force, thereby creating a greater measured impedance at the perimeter of the electrode than at the center of the electrode.

10 Claims, 14 Drawing Sheets

(56) References Cited

OTHER PUBLICATIONS

Gruetzmann et al, "Novel dry electrode for ECGT monitoring", Physiological Measurement 28 (2007), 1375-1390.

Merritt, "Electronic Textile-Based Sensors and Systems for Long-Term Health Monitoring", dissertation submitted to North Carolina State University, Mar. 2008; 175 pages.

Steltenkamp et al, "Electrode structures for acquisition and neural stimulation controlling the cardiovascular system", Sep. 2009, 31st Annual International Conference of the IEEE EMBS, 978-1-4244-3296-7; pp. 5478-5481.

Muhlsteff et al, "Wearable approach for continuous ECG and Activity Patient-Monitoring", Sep. 2004, Proceedings of the 26th Annual International Conference of the IEEE EMBS, 0-7803-8439-3; pp. 2184-2187.

Muhlsteff et al, "Dry electrodes for monitoring of vital signs in functional textiles", Sep. 2004, Proceedings of the 26th Annual International Conference of the IEEE EMBS, 0-7803-8439-3; pp. 2212-2215.

Dias et al, "Non-invasive Iridium Oxide Biopotential Electrodes", 2009, 978-1-4244-4649-0; pp. 1899-1904.

Inoue et al, "Stretchable Human Interface Using a Conductive Silicone Elastomer Containing Silver Fillers", 2009, The 13th IEEE International Symposium on Consumer Electronics (ISCE2009), 978-1-4244-2976-9; pp. 714-717.

\* cited by examiner

SYSTEM AND METHOD FOR A DRY ELASTOMER ELECTRODE

CROSS-REFERENCE TO RELATED PATENTS

The present U.S. Utility Patent Application claims priority as a continuation-in-part of application Ser. No. 13/020,392 (now U.S. Pat. No. 8,569,935), filed Feb. 3, 2011, which is a continuation-in-part of application Ser. No. 12/835,972, filed Jul. 14, 2010, now abandoned, which is a continuation-in-part of application Ser. No. 12/559,061, filed Sep. 14, 2009, now abandoned, which claims benefit of U.S. Provisional Application Ser. No. 61/347,963, filed May 25, 2010, all of which are incorporated by reference herein and made part of the present U.S. Utility Patent Application for all purposes.

This present U.S. Utility Patent Application claims priority to both U.S. Provisional Application Ser. No. 61/788,575, entitled, "SYSTEM AND METHOD FOR A DRY ELASTOMER ELECTRODE," filed Mar. 15, 2013 and U.S. Provisional Application Ser. No. 61/819,574, entitled, "SYSTEM AND METHOD FOR A DRY ELASTOMER ELECTRODE," filed May 4, 2013, all of which are incorporated by reference herein and made part of the present U.S. Utility Patent Application for all purposes.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not applicable.

BACKGROUND OF THE INVENTION

Technical Field of the Invention

This invention relates generally to medical electrodes, and in particular to a low impedance dry stimulation and recording electrode with at least one layer having an elastomeric surface.

Description of Related Art

In the medical field, electrodes are utilized to establish electrical contact with the skin of a patient, and are commonly used for the administration of electrical signals to the patient as well as for receiving electrical signals generated in the body of the patient.

Contact between the electrode and the skin of the patient is typically made through the use of conductive gels, pastes or creams. The conductive gels, pastes or creams are typically applied directly to the surface of the skin of the patient. As can be appreciated, the use of these conductive products can be problematic, as they may produce bridging artifacts, may cause the electrode displacement, i.e., the electrode may slide away from the desired position, or may even dry out rendering the electrode useless and any recording impossible (pertaining mostly to prolonged intraoperative monitoring). The conductive gels, pastes or creams are messy and often irritate the skin of the patient. Another disadvantage of the conductive gels, pastes and creams is that they leave a residue on the skin of the patient subsequent to the removal of the electrode therefrom, thereby requiring additional cleaning of the patient when finished, thus extending the preparation and testing time.

Accordingly, there is a need for systems and methods for providing a dry elastomer electrode that can be utilized in the medical industry without the need for applying conductive gels, pastes or creams to the patient. Dry biocompatible elastomer electrodes are durable, and re-usable. Can be incorporated into fabrics and clothing and can be worn for long periods of time. The rubbery surface of the electrode provides a smooth and uniform contact surface with the skin. Silicon rubber traps moisture (sweat) which helps to reduce the skin-to-electrode impedance, and thereby reduces electrode susceptibility to motion artifacts and noise. On the other hand, traditional wet gel electrodes will not work on the skin of a diaphoretic patient.

BRIEF DESCRIPTION OF THE SEVERAL VIEWS OF THE DRAWINGS

FIG. 8b is a top view of the digital ring electrode a similarly shown in FIG. 8a;

DETAILED DESCRIPTION OF THE INVENTION

Referring now to the figures, wherein various elements depicted therein are not necessarily drawn to scale and wherein, through various views and figures, like elements may be referenced with identical reference numerals, there are illustrated embodiments of a dry elastomer electrode according to the principles of the present invention.

FIGS. 1a-c and FIG. 2 illustrate embodiments of a dry elastomer electrode. The electrodes 1400 (FIGS. 1a and 1c), 1600 (FIG. 1b), and 1800 (FIG. 2) may be a transcutaneous medical electrode for stimulating nerves and/or muscles by generating electricity that could be used in different parts of the body. The electrodes 1400, 1600, and 1800 may be employed for other uses as well. In an embodiment, the electrodes 1400, 1600, and 1800 include a substantially dry body comfortable, biocompatible, electrically conductive interfacing layer of a metal-integral conductive silicon rubber sheet. The dry elastomer electrodes 1400, 1600, and 1800 are employed for similar uses as adhesive electrodes or gel electrodes or where such electrodes may not be appropriate or desirable. For example, the electrodes 1400, 1600, and 1800 may replace an adhesive electrode, e.g. where allergic reaction may be possible.

Figure 1A:
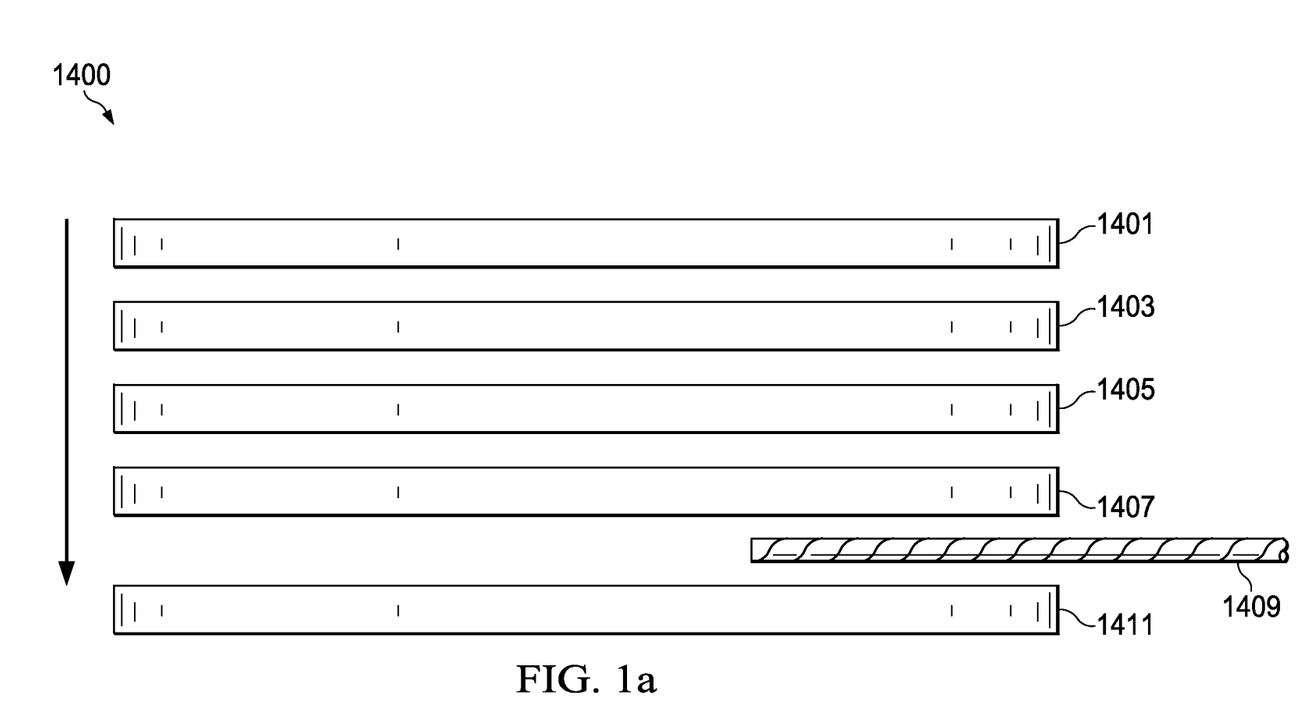
FIG. 1a is an exploded side view of an embodiment of a dry elastomer electrode in accordance with the present invention.
Figure 1B:
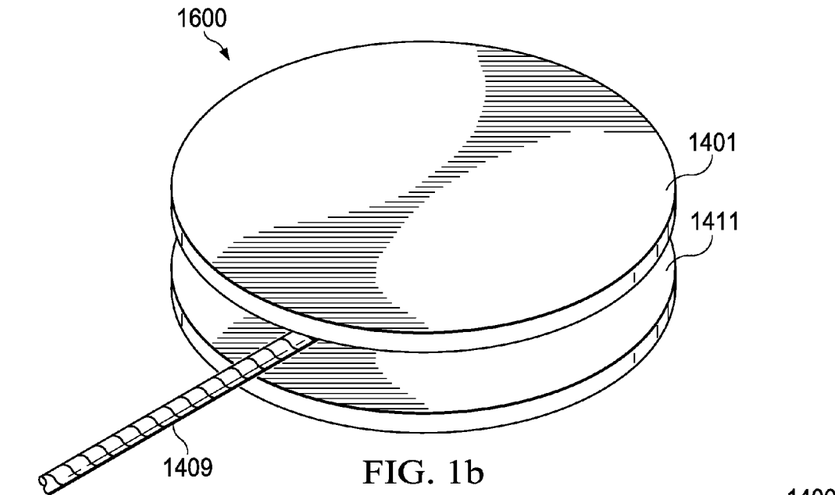
FIG. 1b is an exploded top perspective view of another embodiment of a dry elastomer electrode in accordance with the present invention.
Figure 1C:
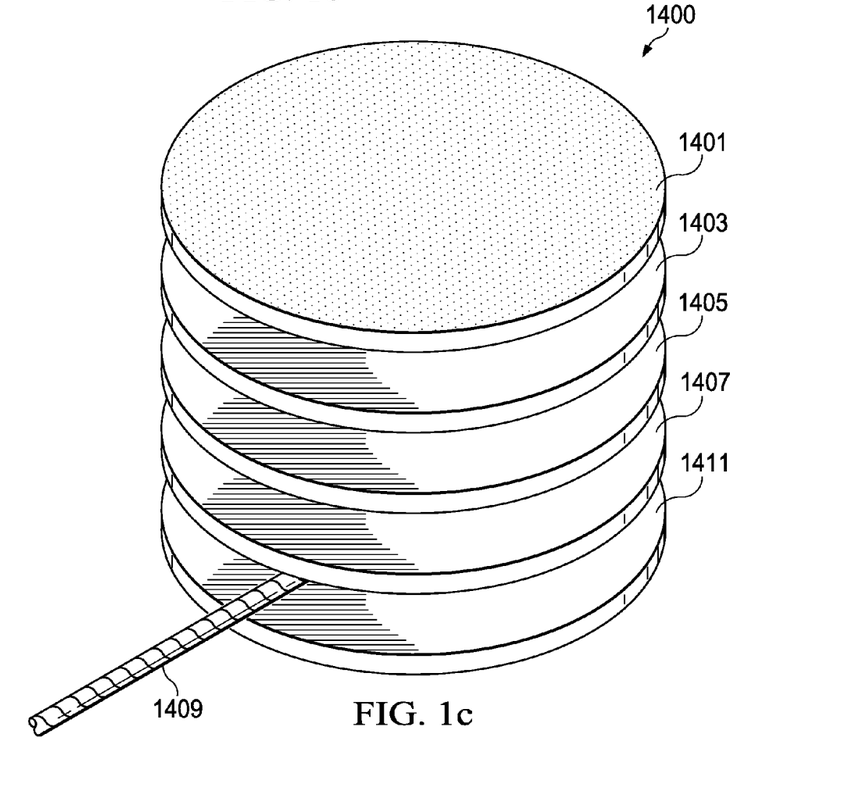
FIG. 1c is an exploded top perspective view of an embodiment of a dry elastomer electrode as similarly shown in FIG. 1a in accordance with the present invention.

FIGS. 1a and 1c illustrate the electrode 1400 which includes in an embodiment at least an upper/first sheet 1401 of metal integral conductive silicon rubber (or elastomer) which, by way of example and not limitation, may be a gold, silver, silver plated copper, or other conductive metal plated material filled silicon. Electrode 1400 further includes a second layer 1403 which may be a conductive adhesive gel layer to adhere to the first sheet 1403, a third sheet 1405 of a conductive carbon film to adhere to the second layer 1403, and a fourth sheet 1407 which may be a conductive metal sheet and the metal may be silver or other appropriate metals. An electrical lead 1409 is positioned and secured between the fourth sheet 1407 and the fifth sheet 1411. The electrical lead 1409 facilitates the delivery of energy to the electrode 1400 from a power source (not shown). Fifth sheet 1411 may be a dielectric/non-conducting flexible backing sheet.

FIG. 1b illustrates the electrode 1600 which includes two layers 1401 and 1411. Electrode 1600 includes an upper/first sheet 1401 of metal integral conductive silicon rubber (or elastomer) which, by way of example and not limitation, may be a gold, silver, silver plated copper, or other conductive metal plated material filled silicon. Electrode 1600 further includes an electrical lead 1409 which is positioned and secured between the first sheet 1401 and the bottom sheet 1411. The electrical lead 1409 facilitates the delivery of energy to the electrode 1600 from a power/recording source (not shown). The bottom sheet 1411 may be a dielectric/non-conducting flexible backing sheet.

Figure 2:
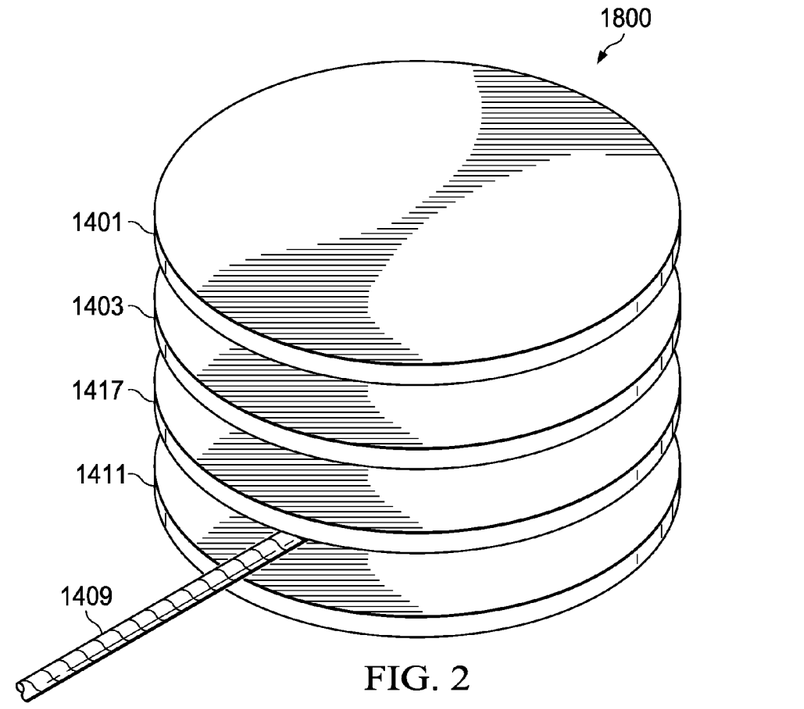
FIG. 2 in an exploded top perspective view of another embodiment of a dry elastomer electrode in accordance with the present invention.
Figure 3:
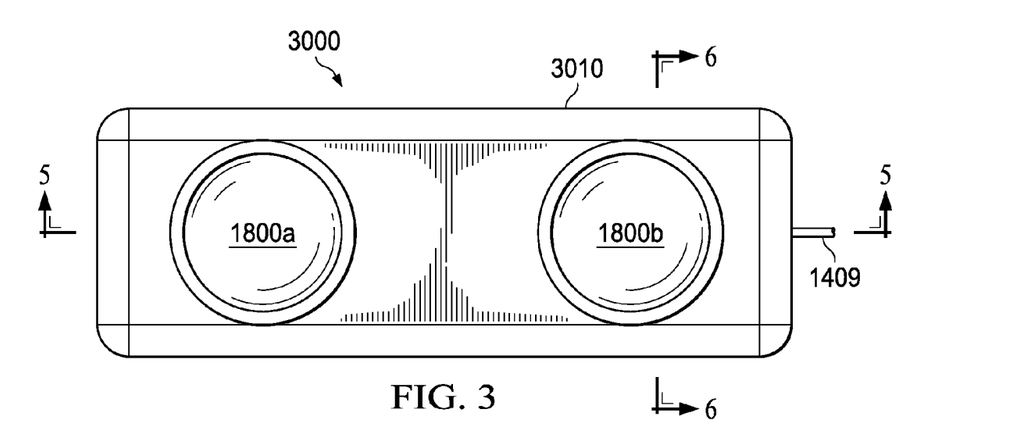
FIG. 3 is a top view of an embodiment of a dry elastomer electrode in a bar electrode in accordance with the present invention.
Figure 4:
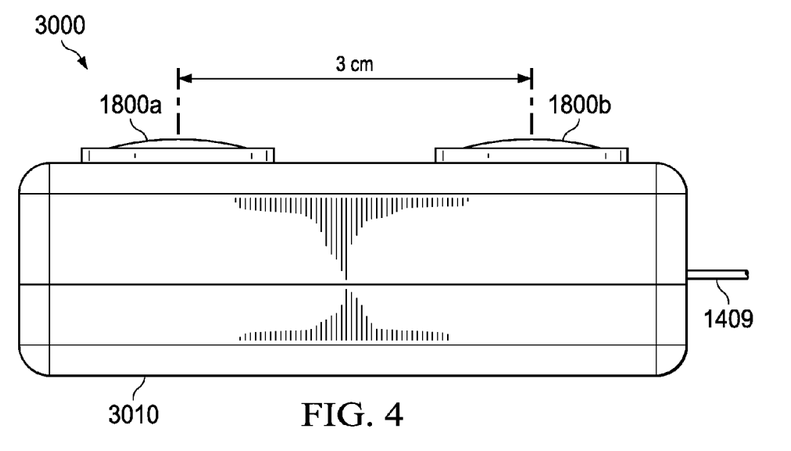
FIG. 4 is a side view of an embodiment of a dry elastomer electrode in a bar electrode as similarly shown in FIG. 3 in accordance with the present invention.
Figure 5:
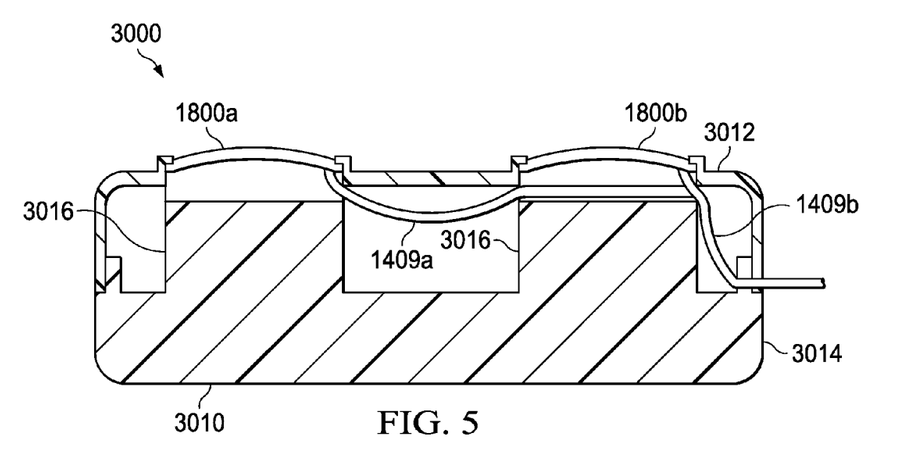
FIG. 5 is a cross-sectional side view taken along line 5-5 of FIG. 3.
Figure 5A:
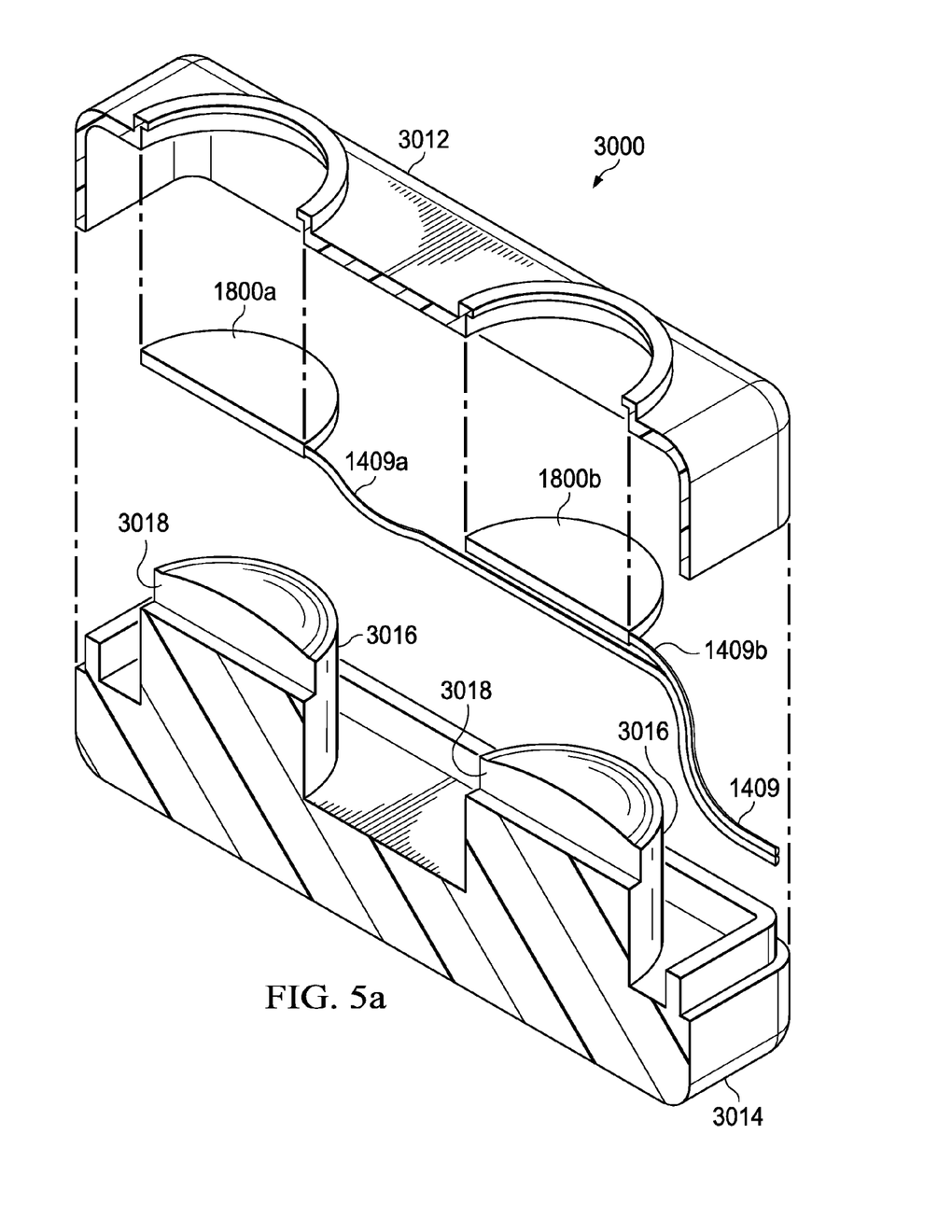
FIG. 5a is an exploded perspective view of the cross-sectional view as similarly shown in FIG. 5.
Figure 5B:
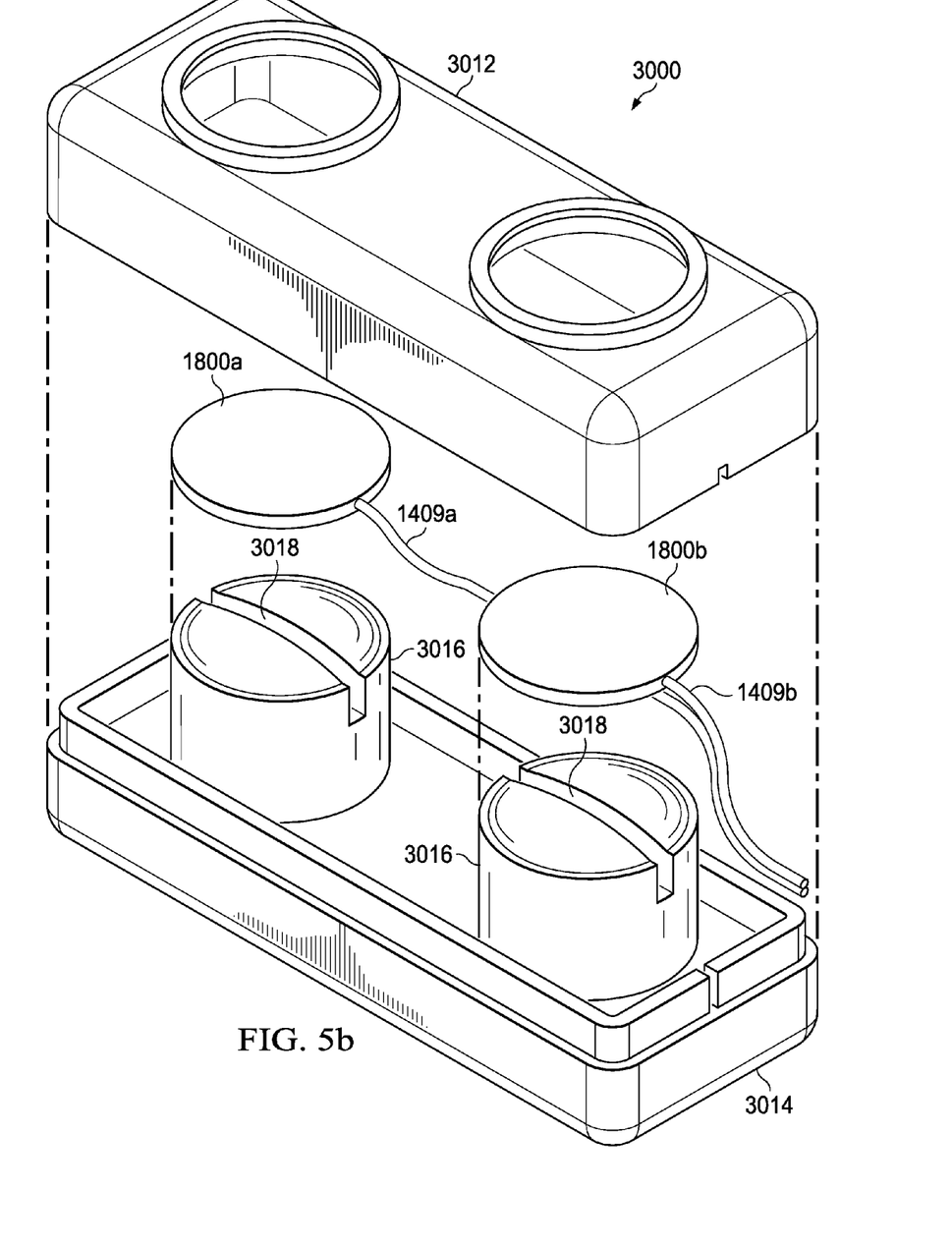
FIG. 5b is an exploded perspective view of an embodiment of a dry elastomer electrode in a bar electrode as similarly shown in FIGS. 3 and 4 in accordance with the present invention.
Figure 6:
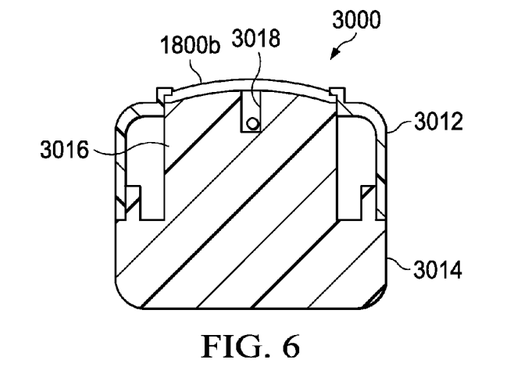
FIG. 6 is a cross-sectional side view taken along line 6-6 of FIG. 3.

FIG. 2 illustrates another embodiment of an electrode 1800 which includes four layers 1401, 1403, 1417 and 1411. The first or top layer 1401 is the interfacing layer and is a silver filled silicone rubber (or elastomer) skin interface. The second layer 1403 is a conductive adhesive layer is positioned in-between first layer 1401 and third layer 1417. The third layer 1417 is an Ag/AgCl film and is positioned between second layer 1403 and fourth layer 1411. The fourth layer 1411 is a dielectric backing layer and is positioned below third layer 1417. An electrical lead 1409 is positioned and secured between the third layer 1417 and the fourth layer 1411. The electrical lead 1409 facilitates the delivery of energy to the electrode 1800 from a power/recording source (not shown).

Though the interfacing or upper layer is described as including the metal integral conductive silicon rubber (or elastomer), other layers may also include the elastomer covering, e.g. conductive inks, or other materials which may facilitate the prevention of corrosion. In addition, one or more other interfacing or upper layers may be added on top of the metal integral conductive silicon rubber (or elastomer) for interfacing with the skin. In another embodiment a plurality of metal integral conductive silicon rubber (or elastomer) layers may be used.

The elastomer is preferably a conductive material with low volume resistivity, such as silicone rubber.

In an embodiment, a dry and flexible electrode is prepared by stacking the desired layers as described herein and pressing them. For the interfacing or top layer 1401, an electrically conductive silicone elastomer containing silver fillers is utilized. Then a pressure is applied to the electrode. The amount of pressure applied to the electrode layers depends upon the desired operating parameters for the electrode for a particular user.

Figure 11:
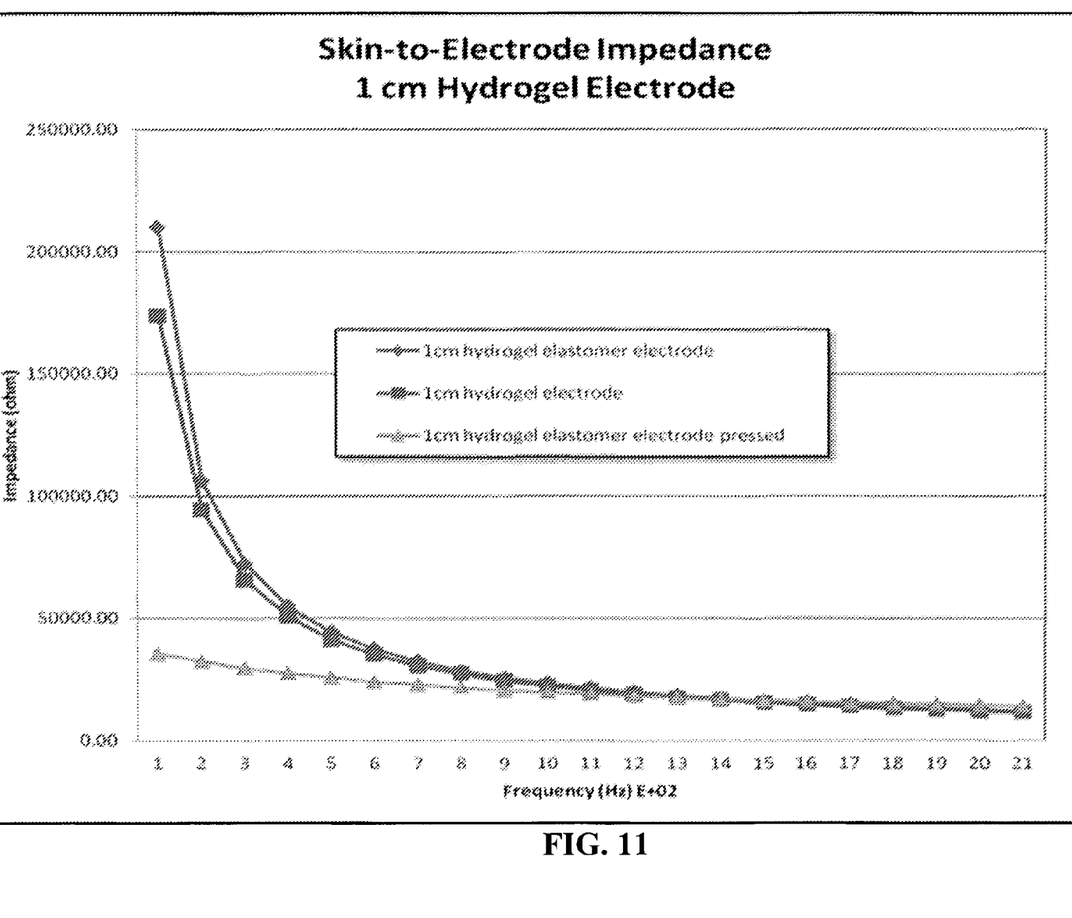
FIG. 11 illustrates a graph of skin to electrode impedance for an embodiment of a Hydrogel Electrode.
Figure 12:
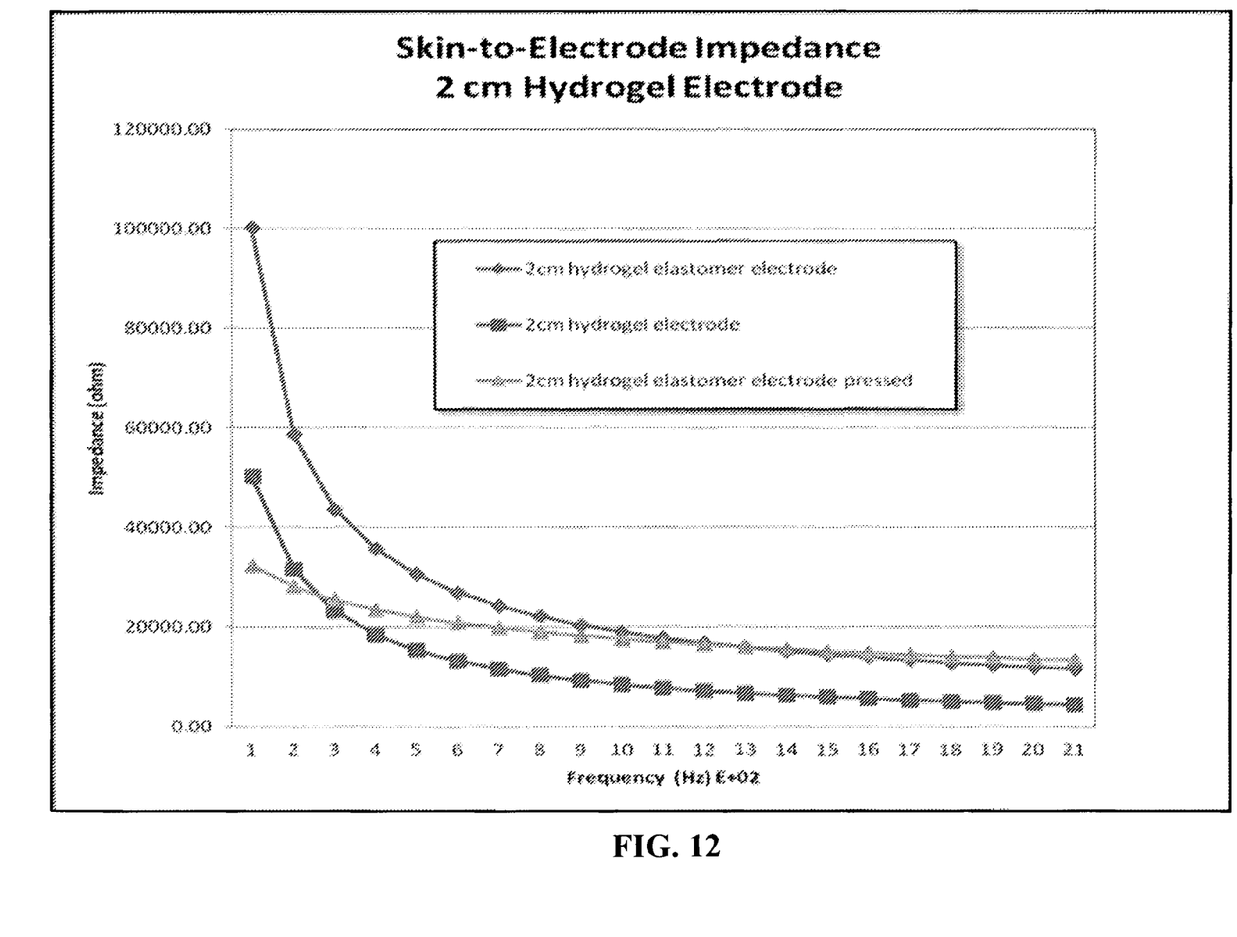
FIG. 12 illustrates a graph of skin to electrode impedance for another embodiment of a Hydrogel Electrode.
Figure 13:
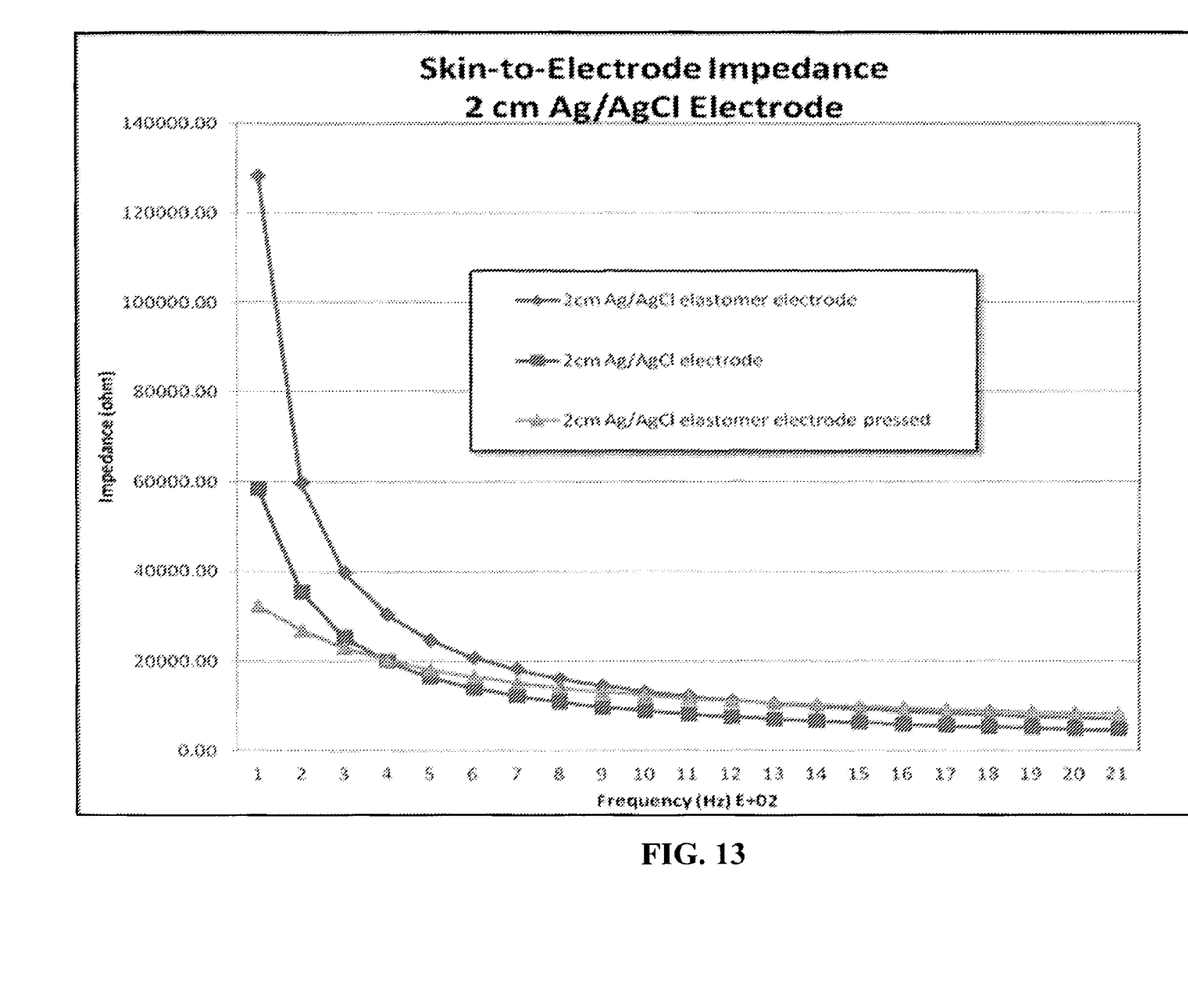
FIG. 13 illustrates a graph of skin to electrode impedance for an embodiment of an Ag/AgCl Electrode.
Figure 14:
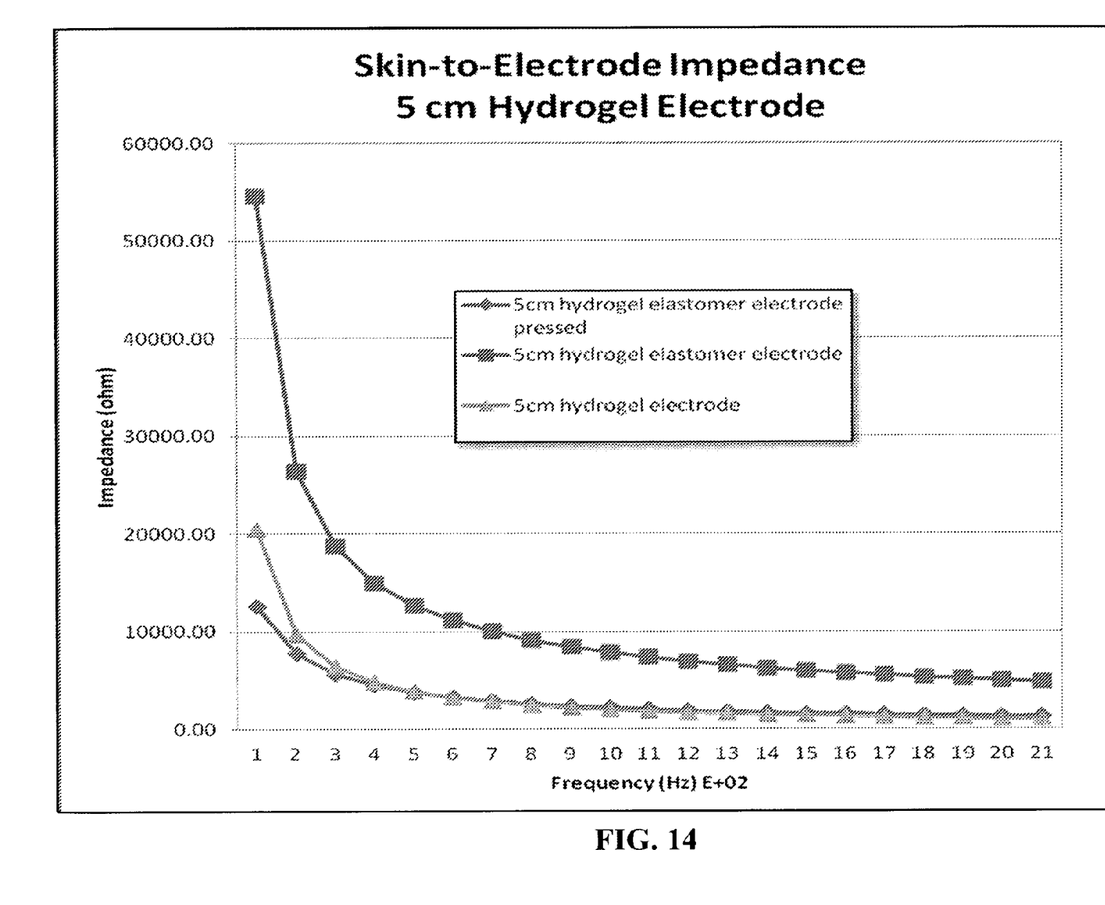
FIG. 14 illustrates a graph of skin to electrode impedance of another embodiment of a Hydrogel Electrode.

FIG. 11 illustrates a graph of skin to electrode impedance for an embodiment of a Hydrogel Electrode. FIG. 12 illustrates a graph of skin to electrode impedance for another embodiment of a Hydrogel Electrode. FIG. 13 illustrates a graph of skin to electrode impedance for an embodiment of an Ag/AgCl Electrode. FIG. 14 illustrates a graph of skin to electrode impedance of another embodiment of a Hydrogel Electrode. For example, in an embodiment, the pressure was approximately 429 PSI for a 5 cm (diameter) electrode and as high as approximately 2684 PSI for a 2 cm electrode and at approximately 11914 PSI for a 1 cm electrode though other pressures may facilitate optimal operation as well, as evidenced by the reduced electrode-skin impedance values. In an embodiment, lower electrode-skin impedance values were found as shown in FIGS. 11-14. FIGS. 11-14 illustrate how compression after laminating changes impedance of elastomer electrodes.

As seen in FIGS. 11-14, different values of impedance are observed, with pressure applied to an electrode, at different frequency ranges. In an embodiment, the pressure applied to an electrode is adjusted during manufacture to try to achieve a certain impedance for a desired frequency range. For example, as shown in FIG. 14, a 5 cm elastomer-hydrogel electrode with pressure applied has a lower impedance than similar hydrogel electrode, only at lower frequencies, and a much lower impedance than elastomer-hydrogel electrode that has been laminated but not pressed, across the entire frequency range. Similarly, as shown in FIG. 11, for a 1 cm elastomer-hydrogel electrode operating at a lower frequency range, more pressure may be applied during manufacture to the elastomer-hydrogel electrode to obtain a lower impedance value for that frequency range while less pressure is applied to a 1cm elastomer-hydrogel electrode that is operating in a higher frequency range. Thus, pressure applied during manufacturing of an electrode is adjusted to attempt to optimize performance of the electrode at a required or desired frequency value.

In an embodiment, to mitigate the "edge effect" and to provide even current density distribution across the electrode, a given electrode is pressed concentrically, where increasingly higher force is applied from the periphery toward the center of the electrode, and thus creating a "segmented impedance" electrode or a varying impedance electrode with the higher impedance at the periphery of the electrode and the lowest resistance in the center of the electrode. For example with an electrode having at least 2.5 cm radius, the following could be utilized to create a "segmented impedance" electrode:

i. 2.5 cm radius is pressed with 500 PSI, then
ii. 2.0 cm radius is pressed with 2000 PSI, then
iii. 1.5 cm radius is pressed with 4000 PSI, then
iv. 1.0 cm radius is pressed with 8000 PSI, then
v. 0.5 cm radius is pressed with 12000 PSI.

Other radii and/or pressures applied to the electrode may be implemented in addition to or alternatively to those shown above. In an embodiment, the electrode has the physical structure of the electrode described herein. In another embodiment, the concentrically applied pressure may be used with an electrode having similar or other physical structures and shapes as well.

Although illustrated hereinabove in the various embodiments as circular shaped electrodes, it is contemplated that the present invention is not limited to circular shaped electrodes, rather the electrodes of the present invention could be of virtually any shape and size with the applied pressure varying from the outer most perimeter to the middle portions so as to provide a selected performance for a particular user.

FIGS. 3-10 illustrate various embodiments of form factors for use of the multilayered dry elastomer electrode as described herein above with respect to FIGS. 1a, 1b, 1c, and 2. Although FIGS. 3-10 are illustrated with a single embodiment of the electrode, it is contemplated that any of the electrode embodiments described herein could be utilized and be within the scope of this invention. It is further contemplated to be within the scope of this invention that other form factors and embodiments may also employ the multilayered dry elastomer electrode.

Referring now to FIGS. 3-6, there is illustrated an embodiment of a bipolar stimulator bar electrode 3000 utilizing multilayered dry elastomer electrodes described hereinabove. Typically bar electrodes are attachable to a stimulator device or electromyographic (EMG) device (not shown) and are utilized for skin or surface stimulation of peripheral nerves. It can be configured with to perform both as a stimulation electrode and a recording electrode, to record nerve and muscle action potentials and to provide electrical stimulation.

Bar electrode 3000 includes an elongated body 3010 having a top 3012 and a bottom 3014. Two cylindrical shape posts 3016 having convex upper surfaces extend up from bottom 3014. Each of posts 3016 have a slot 3018 extending there-across. An electrode, such as described herein above, 1800a and 1800b are placed across the top surfaces of posts 3016 and are positioned between top 3012 and bottom 3014. Electrodes 1800a and 1800b conform to the convex shape of the top surfaces of posts 3016. Holes in top 3012 that are positioned in alignment of posts 3016 in top 3012 permit at least a portion of the electrodes 1800a and 1800b to extend above top 3012 (see FIGS. 4 and 5).

The slots 3018 of each of the posts 3016 are configured in shape to receive the leads 1409a and 1409b of electrodes 1800a and 1800b, respectively. This facilitates the leads 1409 to extend from the bar electrode and ultimately be connected to the stimulator device (not shown).

Figure 7:
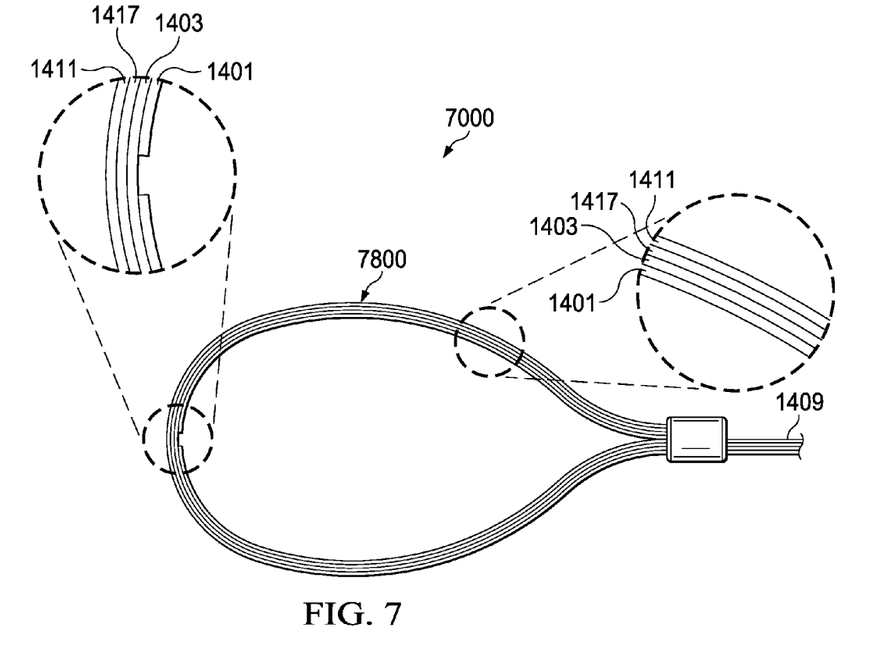
FIG. 7 is a top view of a digital ring electrode with portions enlarged.
Figures 8, 8A:
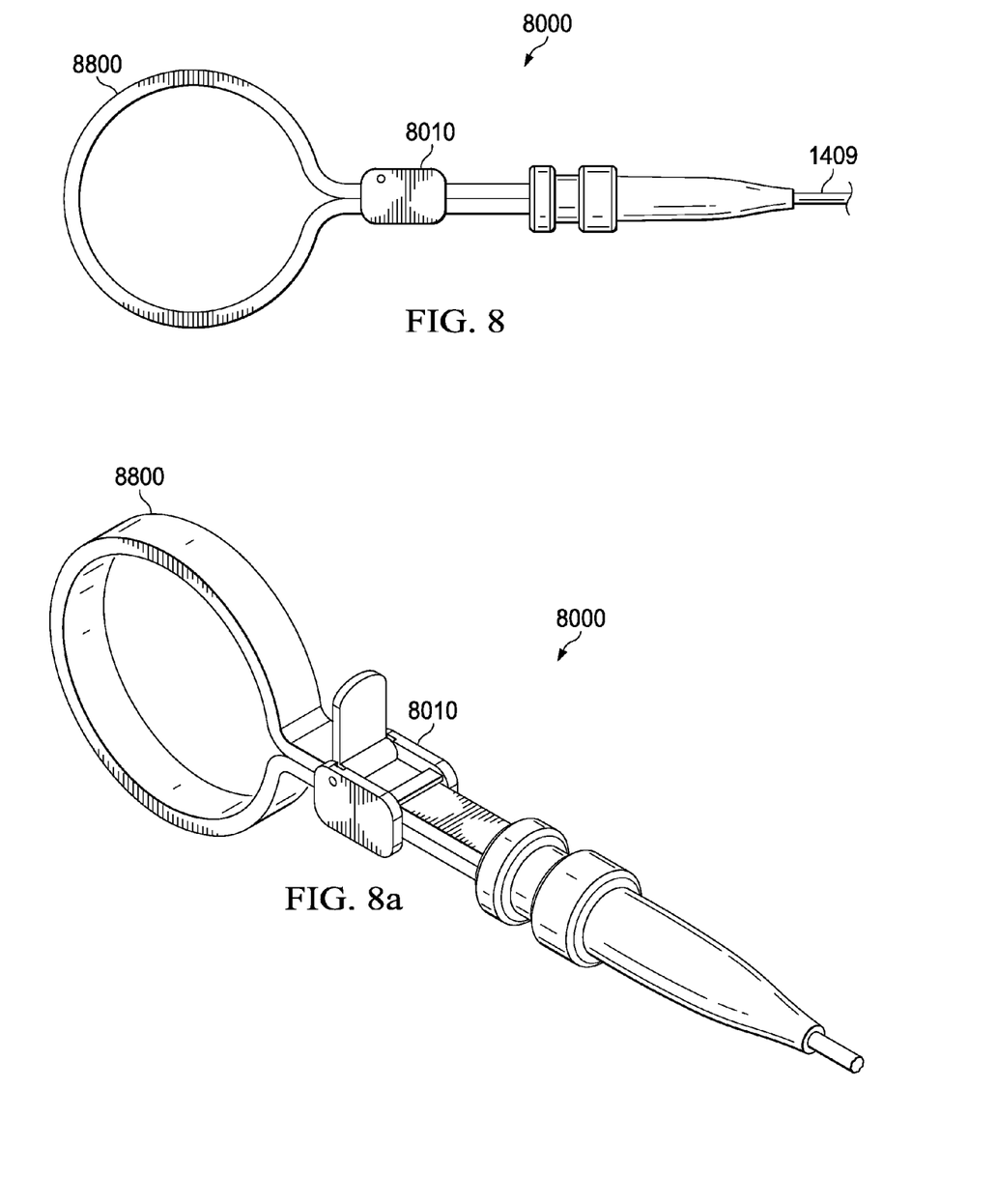
FIG. 8 is a top view of an another embodiment of a digital ring electrode with a clip.
FIG. 8a is a perspective view of a digital ring electrode with a clip as similarly shown in FIG. 8 with the clip in an open position.
Figure 8B:
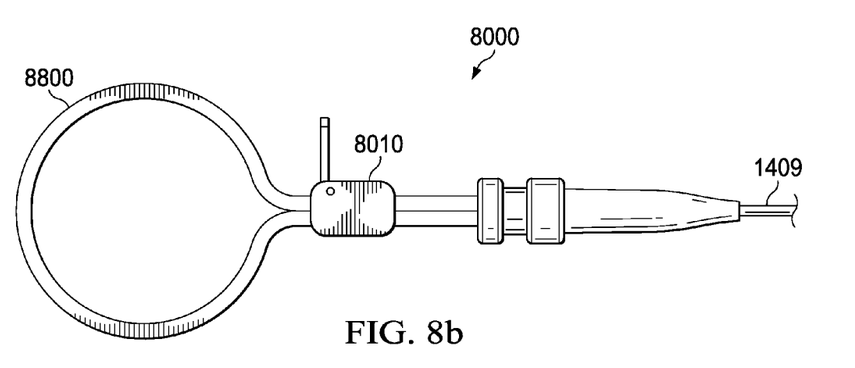
Figure 8C:
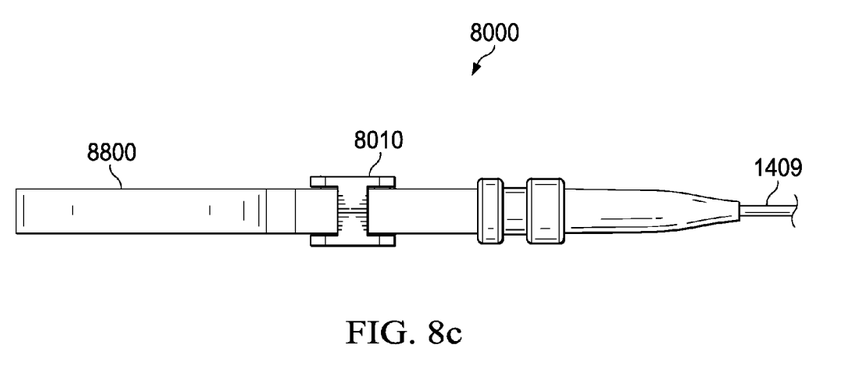
FIG. 8c is a side view of the digital ring electrode as similarly shown in FIG. 8.

Referring now to FIGS. 7-8c, there are illustrated examples of digital ring electrodes employing multilayered dry elastomer electrodes in accordance with the principles of the present invention as described herein. It is contemplated that the embodiments of the digital ring electrodes illustrated in FIGS. 7-8c may be the same with the exception that the embodiment disclosed in FIG. 8 may employ a clip or cord lock as discussed in more detail herein below. As can be appreciated, digital ring electrodes are often used for sensory nerve stimulation or recording from the fingers and toes of patients.

Referring now to FIG. 7, there is illustrated an embodiment of noose type digital ring electrodes 7000. The ring electrode portion 7800 is a multilayered dry elastomer electrode as similarly described herein, with the inner most layer 1401 being silver filled silicone rubber. The next layer 1403 is a conductive adhesive layer, while the third layer 1417 is an Ag/AgCl film, while the outer layer 1411 is a dielectric backing layer. Layer 1401 has a gap or plurality of gaps preventing delaminating while adjusting either the radius or diameter to the given size.

Referring now to FIGS. 8, 8a, 8b and 8c, there is illustrated another embodiment of another digital ring electrode 8000. The ring electrode portion 8800 is a multilayered dry elastomer electrode as described in the various electrode embodiments herein. Digital ring electrode 8000 includes a clip 8010 (or cord lock—not shown) which facilitates the adjustment of the size of the electrode portion 8800. When in the clip 8010 (or cord lock—not shown) is in the open position (FIGS. 8a and 8b), the inner diameter of the electrode 8800 can be adjusted to facilitate the placement of the electrode 8800 onto a finger or toe of a patient and then adjusted to the proper size to secure the electrode 8800 in place. When clip 8010 (or cord lock—not shown) is in the closed position (FIG. 8), the size of the inner diameter of the electrode 8800 cannot be adjusted, thereby keeping the electrode 8800 in place the testing of the patient.

Figure 9:
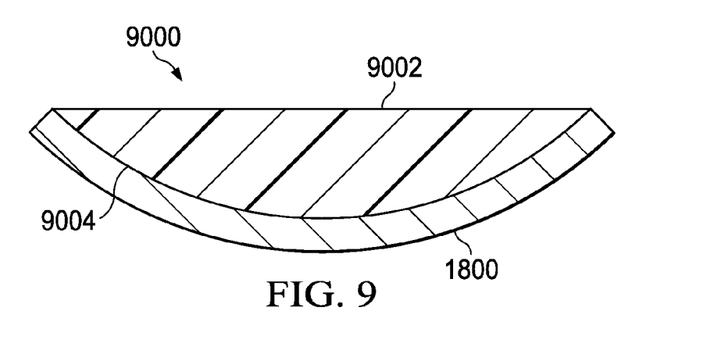
FIG. 9 is a partial cross-sectional view of an electrode with a disc as a backing layer where the electrode conforms to the convex shape of the disc.
Figure 10:
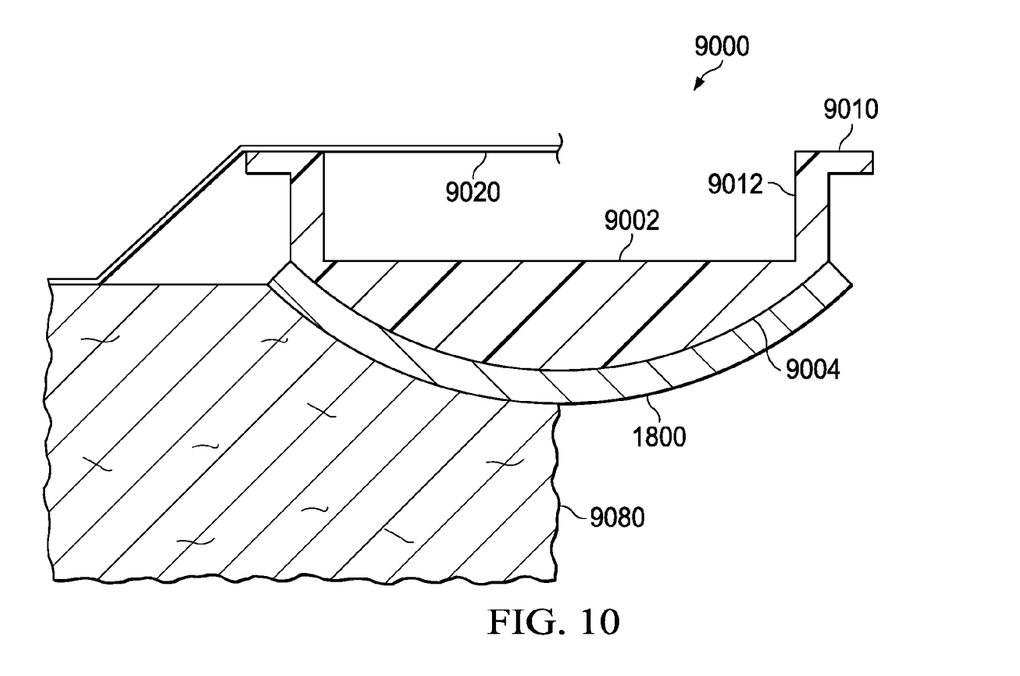
FIG. 10 is a partial cross-sectional view of an electrode with a disc as a backing layer where the electrode conforms to the convex shape of the disc providing uniform contact with the skin.

Referring now to FIGS. 9 and 10, there is illustrated an embodiment of disc electrode 9000 employing multilayered electrodes in accordance with the principles of the present invention as described herein, such as, but not limited to electrode 1400, 1600, and 1800. As illustrated disc electrode 9000 includes a disc 9002 having a convex outer surface 9004, a cylindrical wall 9012 and a flange 9010. An electrode 1800 is attached to the convex surface 9004 of disc 9002 for placement providing uniform contact against the patient's skin 9080. An adhesive 9020 can be utilized to secure the disc electrode 9000 to the patient during use.

The specification has described, at least in part, one or more embodiments. The one or more embodiments described are used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While particular combinations of various functions and features of the present invention have been expressly described herein, other combinations of these features and functions are likewise possible. The present invention is not limited by the particular examples disclosed herein and expressly incorporates these other combinations.

What is claimed is:

1. A device for facilitating at least one of stimulation and recording on the skin of a patient, comprising:
   at least one dry electrode having a perimeter and a center, the at least one dry electrode including a plurality of layers, with a first layer of the at least one dry electrode comprising a metal integral conductive silicon rubber material, wherein the first layer positioned most proximate to the patient is configured to conduct an electrical stimulation signal to the patient;
   the at least one dry electrode including a second layer comprising a dielectric material; and
   a conductive lead positioned intermediate the first layer and the second layer of the dry electrode, the conductive lead for connection to a stimulation device for receiving the electrical stimulation signal.

2. The device of claim 1, wherein the plurality of layers of the at least one dry electrode are compressed together.

3. The device of claim 2, wherein the plurality of layers of the at least one dry electrode are compressed together during manufacture.

4. The device of claim 1, wherein the plurality of layers of the at least one dry electrode are compressed together using a first compression force at the perimeter and a second different compression force at the center.

5. The device of claim 4, wherein the first compression force at the perimeter is lesser that the compression force at the center.

6. The device of claim 5, wherein the at least one dry electrode includes a third layer positioned intermediate the first and second layer, the third layer comprising a conductive gel material.

7. The device of claim 6, and further including a second electrode, with each of the at least one dry electrode and second electrode positioned in a bar electrode configuration.

8. The device of claim 7, wherein the second electrode includes a second conductive lead for connection to a recording device.

9. The device of claim 8, wherein the stimulation device and the recording device are included in a same source.

10. The device of claim 1, wherein the at least one dry electrode has a property of an impedance at the perimeter greater than the impedance at the center.

* * * * *

UNITED STATES PATENT AND TRADEMARK OFFICE
CERTIFICATE OF CORRECTION

PATENT NO. : 9,586,038 B1
APPLICATION NO. : 14/019114
DATED : March 7, 2017
INVENTOR(S) : Tomasz Kosierkiewicz Page 1 of 1

It is certified that error appears in the above-identified patent and that said Letters Patent is hereby corrected as shown below:

In the Specification

In Column 3, Line 24: replace "silicon" with --silicone--

In Column 3, Line 33: replace "silicon" with --silicone--

In Column 3, Line 36: replace "silicon" with --silicone--

In Column 3, Line 50: replace "silicon" with --silicone--

In Column 3, Line 53: replace "silicon" with --silicone--

In Column 4, Line 8: replace "silicon" with --silicone--

In Column 4, Line 13: replace "silicon" with --silicone--

In Column 4, Line 15: replace "silicon" with --silicone--

In the Claims

In Column 7, Line 7, Claim 1: replace "silicon" with --silicone--

Signed and Sealed this
Twenty-fifth Day of April, 2017

Michelle K. Lee
*Director of the United States Patent and Trademark Office*